(12) United States Patent
Herlihy et al.

(10) Patent No.: US 7,452,921 B2
(45) Date of Patent: Nov. 18, 2008

(54) PIPERAZINE-BASED SENSITISERS

(75) Inventors: Shaun Lawrence Herlihy, Chatham (GB); Brian Rowett, Maidstone (GB); Robert Stephen Davidson, Leicester (GB)

(73) Assignee: Sun Chemical Corporation, Parsippany, NJ (US)

( * ) Notice: Subject to any disclaimer, the term of this patent is extended or adjusted under 35 U.S.C. 154(b) by 12 days.

(21) Appl. No.: 10/567,310

(22) PCT Filed: Jul. 2, 2004

(86) PCT No.: PCT/US2004/021370

§ 371 (c)(1),
(2), (4) Date: Nov. 29, 2006

(87) PCT Pub. No.: WO2005/007637

PCT Pub. Date: Jan. 27, 2005

(65) Prior Publication Data

US 2007/0066700 A1    Mar. 22, 2007

(30) Foreign Application Priority Data

Jul. 4, 2003 (GB) ................................. 0315774.0

(51) Int. Cl.
*C08F 2/46* (2006.01)
*C08F 2/50* (2006.01)
*C08J 3/28* (2006.01)
*C08J 7/04* (2006.01)
*G03F 7/031* (2006.01)
*C09D 11/00* (2006.01)
*G03C 1/00* (2006.01)
*C07D 241/04* (2006.01)
*C07D 295/00* (2006.01)

(52) U.S. Cl. ............... 522/8; 522/16; 522/18; 522/33; 522/34; 523/160; 427/510; 427/511; 430/281.1; 564/342; 564/343; 544/395; 544/399; 544/403

(58) Field of Classification Search ............... 544/395, 544/399, 403; 522/8, 16, 18, 33, 34; 523/160; 427/510, 511; 430/281.1; 564/342, 343

See application file for complete search history.

(56) References Cited

U.S. PATENT DOCUMENTS 6,022,906 A * 2/2000 Ohwa et al. .................... 522/8

FOREIGN PATENT DOCUMENTS

JP    57142972    * 9/1982

OTHER PUBLICATIONS

Gamlin, et al, cation to anion triplet-triplet energy transfer in crystalline organic salts, Tetrahedron Letters, vol. 37, No. 34, 1996, pp. 6037-6040.
Kwasi Ohemeng et al, "DNA Gyrase Inhibitory and Antimicrobial Activities of Some Diphenic Acid Monohydroxamides," J. Med. Chem., vol. 40, 1997, pp. 3292-3296.

* cited by examiner

*Primary Examiner*—James O. Wilson
*Assistant Examiner*—Erich A Leeser
(74) *Attorney, Agent, or Firm*—Kramer Levin Naftalis & Frankel LLP

(57) ABSTRACT

Compounds of formula (I) where: {$R^1$ is methyl, ethyl, cycloalkyl or optionally substituted aryl; Z is arylene or a group of formula —$(CHR^4)n$-, where $R^4$ is hydrogen, hydroxy or alkyl, and n is a number from 0 to 6; Y is carbonyl or a —$CH_2$— group; Q is a residue of a mono- or polyhydroxyl compound having from 1 to 6 hydroxy groups; and x is a number from 1 to 6; and esters thereof} are useful as sensitizers for use in radiationcurable compositions.

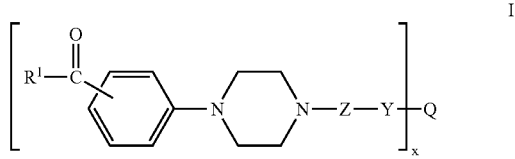

28 Claims, 1 Drawing Sheet

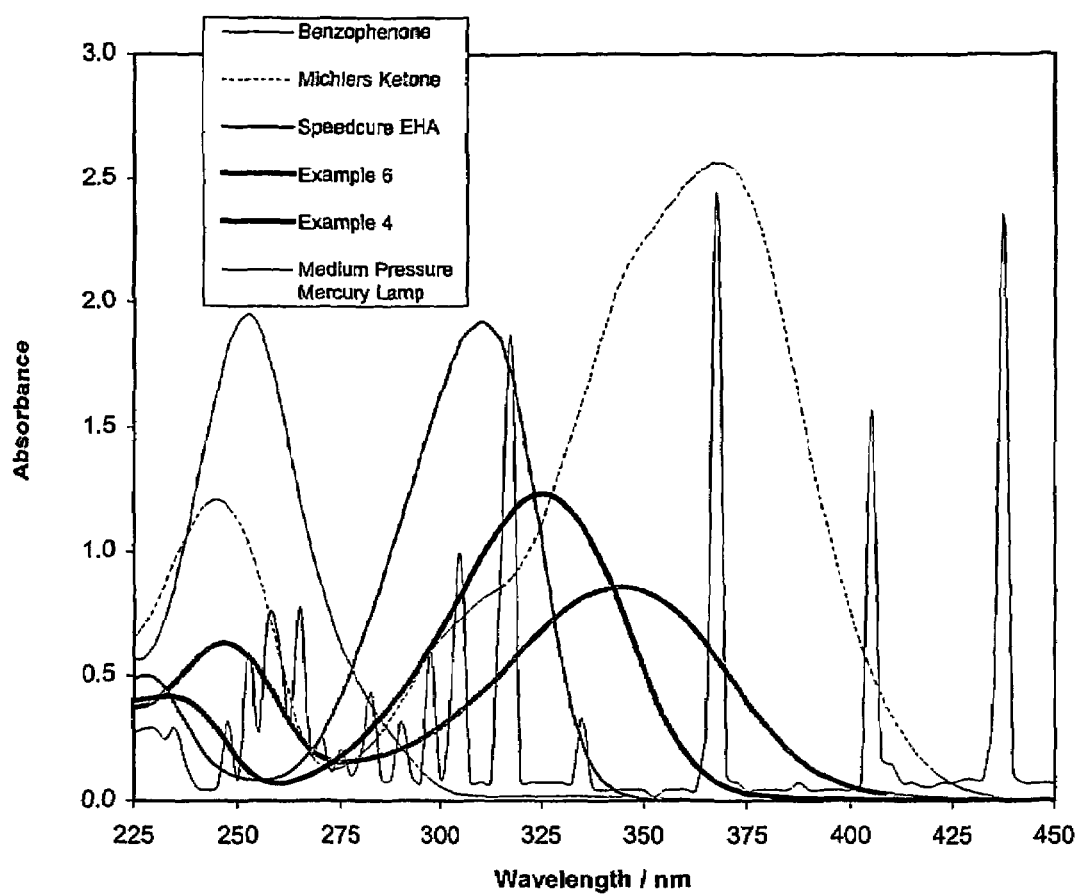

PIPERAZINE-BASED SENSITISERS

FIELD OF THE INVENTION

The present invention relates to a series of new piperazine-based sensitisers for use in radiation curing, for example in the radiation curing of coating compositions such as printing inks or varnishes.

BACKGROUND OF THE INVENTION

Photocurable compositions are cured by exposure to radiation, usually ultraviolet radiation, and include for example, lacquers which may be applied to wood, metal or similar substrates by suitable techniques such as roll coating or curtain coating. They may also be formulated as inks, for example to be applied by techniques such as letterpress, offset lithography, rotogravure printing, silk screen printing, flexographic or ink jet printing. Printing, depending on the particular printing technique, is applicable to a wide range of substrates which include paper, board, glass, plastics materials or metals.

Such compositions will contain the monomer or oligomer to be polymerised, together with a photoinitiator, whose function is to absorb the radiation, and form an excited state which can then initiate polymerisation. In addition, there may be a sensitiser, whose function is to enhance and/or broaden the absorption spectrum of the initiator. Where, as is common, the composition is to be used in liquid form, there may also be a solvent/viscosity modifier, which is preferably also polymerisable. However, it is normally preferred to avoid any such additive, if possible, as it may modify the properties of the final polymerised coating in unpredictable or undesirable ways.

Michler's ketone is the most well-known sensitiser for radiation curing. Although it can function as a photoinitiator in its own right, Michler's ketone is not particularly efficient as it has a significant charge transfer character to its lowest lying triplet state. This makes hydrogen abstraction from donor molecules unfavourable due to the high electron density on the carbonyl oxygen. However, a combination of benzophenone and Michler's ketone acts as a synergistic combination due to the formation of an excited state complex which can be populated by excitation of either molecule.

We have now surprisingly found a series of piperazine compounds which can be used with Type II photoinitiators to provide extremely efficient radiation cure.

Certain compounds similar to those of the present invention have been disclosed in U.S. Pat. No. 6,022,906. However, these are proposed for use as photoinitiators, whereas we have shown that the compounds of the present invention are relatively ineffective as photoinitiators whilst having powerful sensitising activity.

SUMMARY OF THE INVENTION

Thus, the present invention consists in a compound of formula (I):

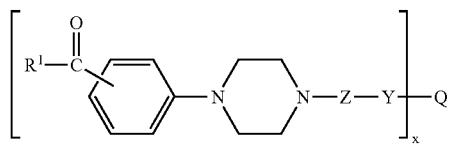

where:
$R^1$ represents a methyl group, an ethyl group, a $C_5$ or $C_6$ cycloalkyl group or a $C_6$-$C_{10}$ aryl group, said aryl group being unsubstituted or being substituted by at least one $C_1$-$C_4$ alkyl or $C_1$-$C_4$ alkoxy group;
Z represents a $C_6$-$C_{10}$ arylene group or a group of formula —(CHR$^4$)$_n$—, where $R^4$ represents a hydrogen atom, a hydroxy group or a $C_1$-$C_4$ alkyl group, and n is a number from 0 to 6;
Y represents a carbonyl group or a —CH$_2$— group, provided that $R^4$ represents a hydroxy group when Y represents a —CH$_2$— group;
Q represents a residue of a mono- or poly-hydroxy compound having from 1 to 6 hydroxy groups; and
x is a number from 1 to 6;
and esters thereof.

The piperazine nitrogen atom adjacent the benzene ring in these compounds has aromatic character, whilst that adjacent the group represented by Z has aliphatic character, thus further improving cure performance when used with Type II photoinitiators.

The present invention also provides an energy-curable composition comprising: (a) a polymerisable monomer, prepolymer or oligomer; (b) a photoinitiator and, optionally, a synergist, and (c) a sensitiser which is a compound of formula (I), or an ester thereof.

The invention still further provides a process for preparing a cured polymeric composition by exposing a composition according to the present invention to curing energy, preferably ultraviolet radiation.

Where $R^1$ represents a $C_5$ or $C_6$ cycloalkyl group, this may be a cyclopentyl or cyclohexyl group.

Where $R^1$ represents a $C_6$-$C_{10}$ aryl group, this may be a phenyl, 1-naphthyl or 2-naphthyl group, which may be unsubstituted or which may have one or more substituents selected from $C_1$-$C_4$ alkyl groups (for example the methyl, ethyl, propyl, isopropyl, butyl, isobutyl, sec-butyl or t-butyl groups) and $C_1$-$C_4$ alkoxy groups (for example the methoxy, ethoxy, propoxy, isopropoxy, butoxy, isobutoxy, sec-butoxy or t-butoxy groups). Of these, we particularly prefer that $R^1$ should be a phenyl group.

Where Z represents an arylene group, this may be a benzene ring, attached at the 1,2-, 1,3- or 1,4-positions, or a naphthalene ring, attached at the 1,2-, 1,3-, 1,4-, 1,5-, 1,6-, 1,7- or 1,8-positions, preferably a benzene ring, attached at the 1,4-positions Where Z represents a group of formula —(CHR$^4$)$_n$—, and $R^4$ represents a $C_1$-$C_4$ alkyl group, the alkyl group may be a methyl, ethyl, propyl, isopropyl, butyl, isobutyl, sec-butyl or t-butyl group, preferably a methyl group.

BRIEF DESCRIPTION OF THE DRAWINGS

FIG. 1 is a graph of light absorbance of photoinitiator components as a function of wavelength of the UV region.

DETAILED DESCRIPTION OF THE INVENTION

In one embodiment of the present invention, Q represents a group of formula -A$_x$-Q', where A represents a group of formula —[O(CHR$^2$CHR$^3$)$_a$]$_y$—, —[O(CH$_2$)$_b$CO]$_y$— or —[O(CH$_2$)$_b$CO]$_{(y-1)}$—[O(CHR$^2$CHR$^3$)$_a$]—; and where:
$R^2$ and $R^3$ are the same or different and each represents a hydrogen atom or a $C_1$-$C_4$ alkyl group;
a is a number from 1 to 2;
b is a number from 4 to 5; and
y is a number from 1 to 10;

x is a number from 1 to 6; and

Q' represents a residue of a mono- or poly-hydroxy compound having from 1 to 6 hydroxy groups.

In the compounds of this embodiment of the present invention, we prefer that A should represent a group of formula —[O(CHR$^2$CHR$^3$)$_a$]$_y$— where a is an integer from 1 to 2, y is as defined above, preferably a number from 3 to 10, and R$^2$ and R$^3$ are the same or different and each represents a hydrogen atom or a C$_1$-C$_4$ alkyl group. More preferably A represents a group of formula —[OCH$_2$CH$_2$]$_y$—, —[OCH$_2$CH$_2$CH$_2$CH$_2$]$_y$— or —[OCH(CH$_3$)CH$_2$]$_y$—, where y is as defined above, preferably a number from 3 to 10, or a group of formula —[O(CH$_2$)$_b$CO]$_y$— or —[O(CH$_2$)$_b$CO]$_{(y-1)}$—[O(CHR$^2$CHR$^3$)$_a$]—, where b is a number from 4 to 5 and R$^2$, R$^3$ and y are as defined above, y preferably being a number from 3 to 10. Still more preferably, y is a number from 3 to 6.

In general, in the compounds of the present invention, y is preferably a number from 3 to 10, more preferably from 3 to 6. We also prefer compounds of this embodiment in which x is 2 and y is a number from 1 to 10.

The compounds of this embodiment of the present invention are preferably of a generally polymeric nature. The polymeric nature may be provided by either the group represented by Q' or the group represented by A or by both.

The polymeric polyhydroxy residue of formula -A$_x$-Q', which forms the core of the compounds of the present invention has a major influence on the behaviour of the compounds. In accordance with the present invention, it is important that it should have a polymeric nature, since the resulting compounds tend to be liquid or of low melting point, thus aiding dispersion in the coating composition. Compounds having a similar structure but not polymeric tend to be solid and/or insoluble in these coating compositions. However, we prefer that the core residue, of formula -A$_x$-Q', should not have too high a molecular weight, and prefer that the residue of formula -A$_x$-Q' should have a molecular weight no greater than 2000, preferably no greater than 1200, still more preferably no greater than 1000, and most preferably no greater than 800.

We particularly prefer that Q' is a residue of a C$_2$-C$_6$ alkylene glycol or of a polyalkylene glycol, in which the alkylene part has from 2 to 6 carbon atoms. More preferably, Q' is a residue of ethylene glycol, propylene glycol, butylene glycol, glycerol, 2,2-propanediol, polyethylene glycol, polypropylene glycol, polybutylene glycol, trimethylolpropane, pentaerythritol or di-pentaerythritol.

It will be appreciated that, when the compounds of the present invention are analysed, the numbers a, b and y in the above formulae need not be integral, and, indeed, it is unlikely that they will be integral, since the compounds of the present invention may be mixtures of several compounds in which the numbers a, b and y differ. In accordance with the present invention, provided that the average value of each of these numbers is as defined above, this will be satisfactory. Of course, for each individual molecule of the compounds of the present invention, a, b and y will be integral, and it might be possible to separate out such individual compounds, but, in practice, mixtures of these compounds are used.

In another preferred embodiment of the present invention, x is 1. In this case, Q is preferably the residue of a compound of formula R$^1$—OH, where R$^1$ is as defined above. More preferably, Q is a C$_1$-C$_6$ alkoxy group or a phenoxy group. We also particularly prefer, in this embodiment, that Z is a phenylene group.

In another preferred embodiment of the present invention, Q is a residue of a C$_2$-C$_6$ polyalkylene glycol, in which the alkylene part has from 2 to 6 carbon atoms. Alternatively, Q may be a bis(C$_1$-C$_6$ hydroxyalkyl) ether, where the two hydroxyalkyl parts may be the same as or different from each other, although they are preferably the same, and each may have one or more hydroxy groups. In this embodiment, Q is preferably a residue of ethylene glycol, propylene glycol, butylene glycol, glycerol, 2,2-propanediol, polyethylene glycol, polypropylene glycol, polybutylene glycol, trimethylolpropane, di-trimethylolpropane, pentaerythritol or di-pentaerythritol.

The compounds of the present invention may be prepared simply, for example by a Michael addition of a compound of formula (II):

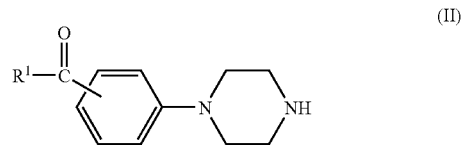

(II)

(in which R$^1$ is as defined above) with an active compound corresponding to the group of formula -(Z-Y)$_x$-Q (where Z, Y, x and Q are as defined above). This active compound may, for example, be a compound including a carbon-carbon double bond or an epoxide group, as illustrated in more detail in the Examples appearing hereafter.

The composition of the present invention may be formulated as a printing ink, varnish, adhesive or any other coating composition which is intended to be cured by irradiation, whether by ultraviolet or electron beam. Such compositions will normally contain at least a polymerisable monomer, prepolymer or oligomer, photoinitiator, amine synergist and the sensitiser of the present invention, but may also include other components well known to those skilled in the art, for example, waxes, flow aids and, in the case of printing inks, a pigment.

The compounds of the present invention will sensitise a wide variety of benzophenone derivative photoinitiators in current use, and the exact nature of the photoinitiator used in the composition of the present invention is, therefore, not particularly critical to the invention, although its choice may well have an important effect on the properties of the cured composition or the ease or extent of cure, as is well known in the art. Examples of such photoinitiators include: benzophenone, 4-methylbenzophenone, 4-phenylbenzophenone and benzophenone 2-methyl ester.

A wide variety of monomers and prepolymers may be subjected to photoinitiation with these photoinitiators, and using the compounds of the present invention as sensitisers, and the nature of the monomers and prepolymers is not critical to the present invention.

The radiation-curable monomer or oligomer is preferably an ethylenically unsaturated compound, for example an acrylate or methacrylate. Examples of suitable acrylate oligomers include aliphatic or aromatic urethane acrylates, polyether acrylates, polyester acrylates and epoxy acrylates (such as bisphenol A epoxy acrylate). Examples of suitable acrylate monomers include hexanediol diacrylate, trimethylolpropane triacrylate, di-trimethylolpropane tetraacrylate, di-pentaerythritol pentaacrylate, polyether acrylates, such as ethoxylated trimethylol propane triacrylate, glycerol propoxylate triacrylate, ethoxylated pentaerythritol tetraacrylate, epoxy acrylates such as dianol diacrylate(=the diacrylate of 2,2-bis[4-(2-hydroxyethoxy)phenyl]propane, Ebecryl 150 from UCB), glycol diacrylates such as tripropylene glycol diacrylate and alkyl acrylates and methacrylates (such as hexanediol diacrylate, isobornyl acrylate, octadecyl acrylate, lauryl acrylate, stearyl acrylate and isodecyl acrylate, and the corresponding methacrylates).

Also, the compositions of the present invention preferably contain a synergist, such as an aminoacrylate or a dimethylaminobenzoic acid ester, as is well known in the art. Preferably the synergist will be a dimethylaminobenzoic acid ester in the case of a printing ink or an aminoacrylate in the case of a varnish. Some inks, such as those used in flexographic printing applications, may contain both amine types.

Although the compositions of the present invention preferably contain a synergist, such as an aminoacrylate, as is well known in the art the use of products of this invention in a well formulated system may also allow the level of standard amine synergists to be reduced or allow them to be eliminated altogether.

The amounts of the radiation-curable monomer or oligomer, photoinitiator, synergist and optional colorant will vary according to the type of varnish or ink, the particular equipment to be used to apply it and the application. However, typically, the amount of photoinitiator plus amine synergist is from 1% to 15-20% by weight of the total composition.

The compounds formula (I) are especially suited for varnishes and inks, especially printing inks, including lithographic inks. These typically comprise, as additional components to those referred to above, one or more of pigments, waxes, stabilisers, and flow aids, for example as described in "Printing Ink Manual", fourth edition, Leach R. H. et al. (eds.), Van Nostrand Reinhold, Wokingham, (1988), the disclosure of which is incorporated herein by reference. Since the compounds of the present invention cause yellowing, they may only be used successfully in varnishes if this is not of importance.

Additives which may be used in conjunction with the principal components of the coating formulations of the present invention include stabilisers, plasticisers, pigments, waxes, slip aids, levelling aids, adhesion promoters, surfactants and fillers. Also other photoinitiators, such as thioxanthone (and derivatives), benzophenone (and derivatives), hydroxyalkylphenones, aminoalkylphenones and anthraquinone (and derivatives) may be included.

The compounds of the present invention may be included as sensitisers in coating formulations such are well known in the art, and the precise composition of such formulations will vary depending upon the other components and the intended use, as is well known. However, a typical formulation for an ink coatable by flexography might be:

| | |
|---|---|
| Pigment | 8-20% |
| Photoinitiator + synergist | 4-10% |
| Monomer/prepolymer/oligomers | 30-90% |
| Additives | 0-10% |
| Sensitiser | 1-5%, | although inks may have compositions outside these ranges as is well known in the art.

The invention is further illustrated by the following non-limiting Examples.

EXAMPLE 1

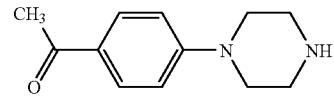

5.0 g of 4-fluoroacetophenone (0.036195 moles), 3.11 g of piperazine (0.036195 moles), 5.21 g of potassium carbonate powder (0.037705 moles) and 25 ml dry dimethyl sulphoxide (DMSO) were mixed in a three necked flask equipped with a stirrer, nitrogen inlet, condenser, calcium chloride drying tube/nitrogen outlet and a temperature probe. The mixture was heated to reflux for a total of 12 hours (~190° C.) under a constant flow of nitrogen gas. The mixture was then cooled to room temperature and the mixture was filtered to remove the inorganics. A further 100 ml of DMSO was used to wash out the reaction flask. The DMSO solution was then added to 100 g of ice. The mixture obtained was extracted with 3×75 ml of dichloromethane. The dichloromethane layers were combined and were washed with 50 ml of saturated sodium chloride solution. The dichloromethane layer was then dried using anhydrous magnesium sulphate. The magnesium sulphate was removed by filtration and the dichloromethane was then removed on a rotary evaporator to yield the crude product. 30ml of water was added to the crude product and the mixture was then filtered to recover the product. The product was washed with a further 100 ml of water and then dried in a vacuum oven at 50° C. for 4 hours.

Product yield 3.05 g (41.25%) of a yellow/orange solid.

The product was analysed by IR, and GC-CIMS.

EXAMPLE 2

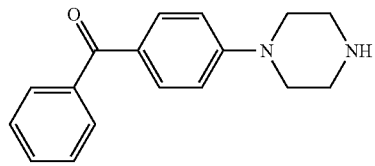

5.0 g of 4-fluorobenzophenone (0.0249737 moles), 2.15 g of piperazine (0.0249737 moles), 3.6 g of potassium carbonate powder (0.0260225 moles) and 50 ml dry DMSO were mixed in a three necked flask equipped with a stirrer, nitrogen inlet, condenser, calcium chloride drying tube/nitrogen outlet and a temperature probe. The mixture was heated to reflux for a total of 12 hours (~190° C.) under a constant flow of nitrogen gas. The mixture was then cooled to room temperature and the mixture was filtered to remove the inorganics. A further 30 ml of DMSO was used to wash out the reaction flask. The DMSO solution was then added to 100 g of water. The mixture obtained was extracted with 3×75 ml of dichloromethane. A further 100 ml of water and approximately 5 g of sodium chloride was added to the separating flask to aid separation. The dichloromethane layers were combined and were washed with 100 ml of saturated sodium chloride solution. The dichloromethane layer was then dried using anhydrous magnesium sulphate. The magnesium sulphate was removed by filtration and the dichloromethane was then removed on a rotary evaporator to yield the product.

Product yield 4.5 g (67.7%) of a yellow/brown paste.

The product was analysed by IR, and GC-CIMS.

EXAMPLE 3

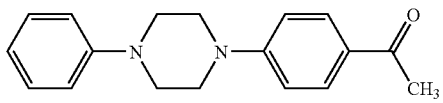

5.0 g of 4-fluoroacetophenone (0.036195 moles), 6.08 g of N-phenylpiperazine (0.036195 moles), 5.21 g of potassium carbonate powder (0.037705 moles) and 50 ml dry DMSO were mixed in a three necked flask equipped with a stirrer, nitrogen inlet, condenser, calcium chloride drying tube/nitrogen outlet and a temperature probe. The mixture was heated to reflux for a total of 12 hours (~190° C.) under a constant flow of nitrogen gas. The mixture was then cooled to room temperature and the mixture was filtered to remove the inorganics. A further 75 ml of DMSO was used to wash out the reaction flask. The DMSO solution was then added to 100 g of water. The mixture obtained was extracted with 3×75 ml of dichloromethane. A further 100 ml of water and approximately 5 g of sodium chloride was added to the separating flask to aid separation. The dichloromethane layers were combined and were washed with 100 ml of saturated sodium chloride solution and then 100 ml of water. The dichloromethane layer was then dried using anhydrous magnesium sulphate. The magnesium sulphate was removed by filtration and the dichloromethane was then removed on a rotary evaporator to yield the product. The solid material obtained was dried in a vacuum oven at 50° C. for 4 hours.

Product yield 2.59 g (25.55%) of a brown solid.
The product was analysed by IR, and GC-CIMS.

EXAMPLE 4

0.715 g of propoxylated neopentyl glycol diacrylate (PN-PGDA, mol. wt. 328) (0.0021786 moles), 1.0 g of 4-piperazinoacetophenone (prepared as described in Example 1) (0.0049019 moles), toluene 20 ml and 0.05 g 1,8-diazabicyclo(5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted 4-piperazinoacetophenone, and then the solvent was removed on a rotary evaporator to yield the product.

Product yield 1.92 g of a viscous slightly yellow liquid.
The product was analysed by IR, HPLC and LCMS.

EXAMPLE 5

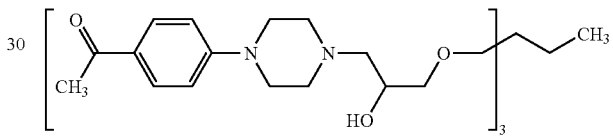

8.11 g Piperazinoacetophenone (0.0396864 moles), 4.00 g trimethylolpropane triglycidyl ether (0.0132288 moles) and toluene 50 ml were mixed in a two-necked flask fitted with a condenser, stirrer and temperature probe. The mixture was heated to reflux for a total of 4 hours. The mixture was then cooled and filtered and then the solvent was removed on a rotary evaporator to yield the product.

Product yield 11.57 g (95.54%) of a viscous slightly yellow liquid.
The product was analysed by IR, HPLC and LCMS.

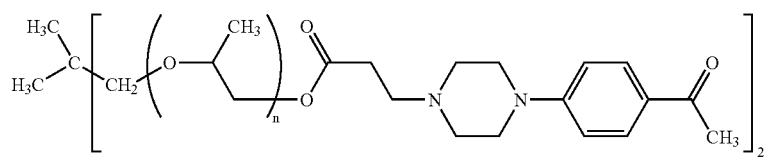

EXAMPLE 6

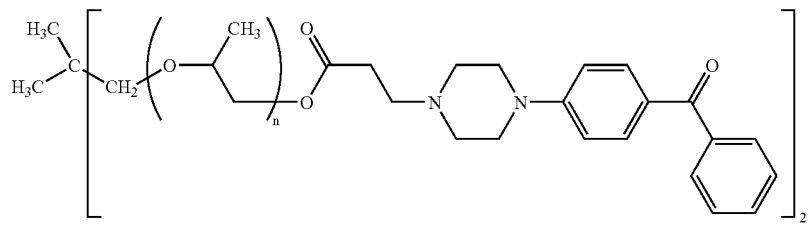

1.64 g Propoxylated neopentyl glycol diacrylate (PN-PGDA, mol. wt. 328) (0.0050124 moles), 3.00 g of the product prepared as described in Example 3 (0.011278 moles), toluene 30 ml and 0.114 g 1,8-diazabicyclo(5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted 4-piperazinobenzophenone and then the solvent was removed on a rotary evaporator to yield the product.

Product yield 4.96 g of a viscous brown liquid.

The product was analysed by IR, HPLC and LCMS.

EXAMPLE 7

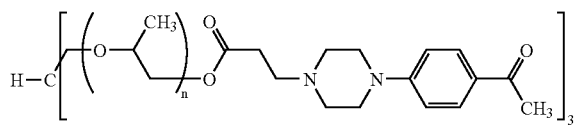

4.08 g 4-Piperazinoacetophenone (0.02 mols) and 3.84 g glycerol propoxylate triacrylate (0.008 moles) were refluxed in 100 ml acetonitrile with 0.02 g butylated hydroxytoluene stabiliser for 3 hours. 0.2 g of the tertiary amine catalyst DABCO was added and the solution was stirred at 40° C. for approximately two weeks. After cooling, the solution was filtered and all solvent removed on a rotary evaporator to give a pale yellow high viscosity liquid.

Product yield=7.54 g

The product was analysed by IR, HPLC and H¹NMR.

EXAMPLE 8

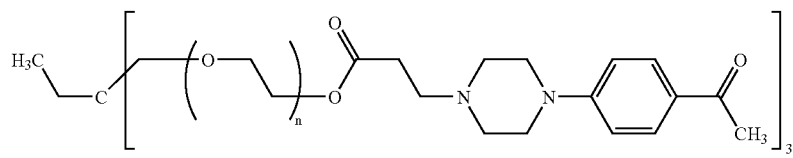

4.59 g Piperazinoacetophenone (0.0225 moles), 3.6 g trimethylolpropane ethoxylate triacrylate (0.0075 moles) 0.02 g butylated hydroxytoluene stabiliser and 0.2 g DABCO catalyst were refluxed in 100 ml toluene for a total of 29 hours. After cooling, the solution was filtered and all solvent removed on a rotary evaporator to give a pale yellow high viscosity liquid.

Product yield=7.88 g

The product was analysed by IR, HPLC and H¹-NMR.

EXAMPLE 9

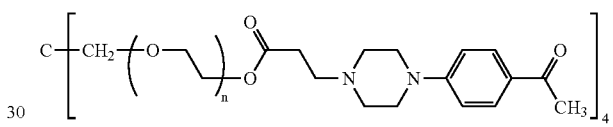

4.08 g Piperazinoacetophenone (0.02 moles) and 2.44 g pentaerythritol ethoxylate tetraacrylate were heated to reflux for a total of 40 hours in 100 ml toluene using 0.1 g DABCO catalyst. After cooling, the solution was filtered and all solvent was removed on a rotary evaporator to give a pale yellow high viscosity yellow liquid.

Product yield=6.27 g

The product was analysed by IR, HPLC and H¹NMR.

EXAMPLE 10

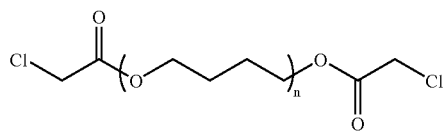

18.9 g Chloroacetic acid (0.2 moles) and 25 g polytetrahydrofuran (0.1 moles, 250 molecular weight) were azeotropically refluxed for 3.5 hours in 200 ml toluene using 0.5 g p-toluenesulphonic acid as a catalyst and 0.1 g butylated hydroxytoluene as a stabiliser. The solution was cooled and all solvent removed in a rotary evaporator to yield a low viscosity colourless liquid.

Product yield=43.3 g

The product was analysed by IR.

EXAMPLE 11

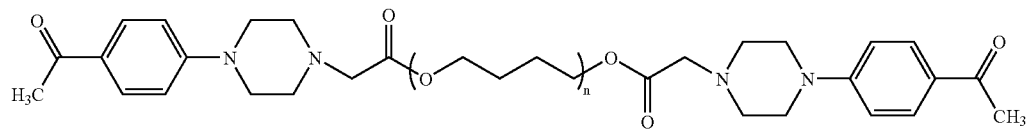

4.28 g Piperazinoacetophenone (0.021 moles), 2.22 g triethylamine (0.022 moles) and 100 ml toluene was stirred at room temperature and a solution of 4.07 g of the product of Example 10 (0.01 moles) in 50 ml toluene was slowly added over 30 minutes with stirring. Reaction temperature was raised to 60° C. for 6 hours but the reaction progress was slow. 2.0 ml pyridine (0.022 moles) were added and the solution temperature raised to 100° C. for 6 hours. After cooling to room temperature, the liquid was decanted off and washed twice with 100 ml deionised water. After drying over anhydrous magnesium sulphate, all solvent was removed on a rotary evaporator to give a dark orange/brown liquid, which later solidified to a pasty solid.

Product yield=5.58 g

The product was analysed by IR and HPLC.

EXAMPLE 12

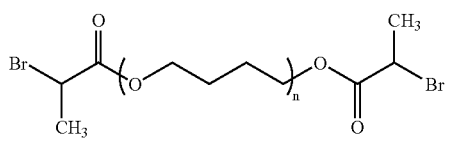

79.8 g 2-Bromopropionic acid (0.325 moles) and 36.98 g polytetrahydrofuran (0.148 moles, 250 molecular weight) were azeotropically refluxed for 4 hours in 300 ml toluene using 0.75 g p-toluenesulphonic acid as a catalyst and 0.15 g butylated hydroxytoluene as a stabiliser. The solution was washed twice whilst still hot with 100 ml 10% aqueous potassium carbonate solution and twice with 100 ml deionised water before azeotroping to dryness and removing all solvent on a rotary evaporator to yield a colourless low viscosity liquid.

Product yield=77.2 g

The product was analysed by IR.

EXAMPLE 13

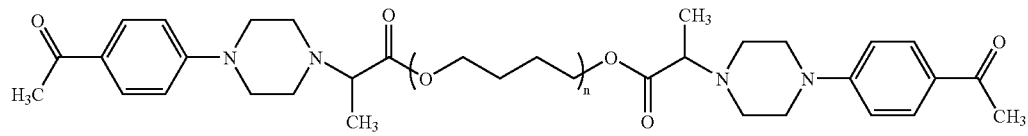

4.28 g Piperazinoacetophenone (0.021 moles), 3.14 g tripropylamine (0.022 moles), 4.96 g of the product prepared as described in Example 12 (0.01 moles), 0.1 g of the tertiary amines catalyst DABCO and 150 ml toluene were heated to reflux for 15 hours. After cooling to room temperature, the liquid was filtered and washed twice with 150 ml deionised water. After drying over anhydrous magnesium sulphate, all solvent was removed on a rotary evaporator to give a light brown high viscosity liquid.

Product yield=5.98 g

The product was analysed by IR and HPLC.

EXAMPLE 14

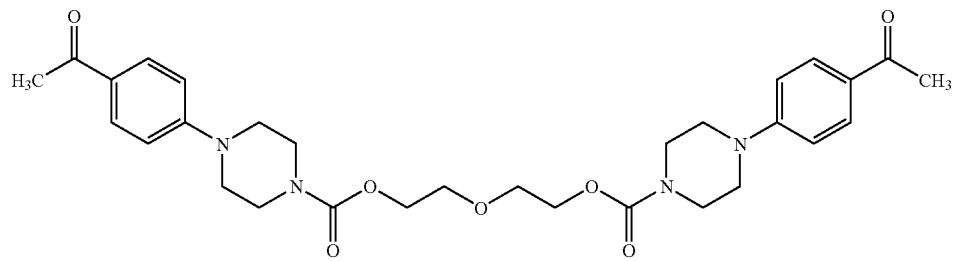

5.0 g of 4-piperazinoacetophenone (0.02451 moles), 2.48 g of triethylamine (0.02451 moles) and 75 ml of toluene were mixed in a two necked flask equipped with a stirrer, condenser and a temperature probe. 2.635 g of diethylene glycol chloroformate (0.012255 moles) in 20 ml of toluene were then added slowly, ensuring the exotherm was controlled (temperature maximum throughout the addition was 42° C.). After the addition was complete, the mixture was stirred for 2 hours, allowing the mixture to cool to room temperature. The mixture was then filtered to remove the insoluble triethylamine hydrochloride formed during the reaction. The toluene was then removed on a rotary evaporator to yield the product.

Product yield 6.78 g of a white solid.

The product was analysed by IR, HPLC and LCMS.

EXAMPLE 15

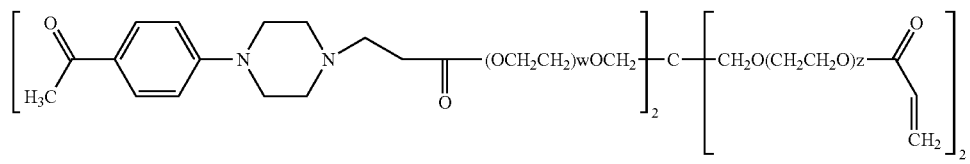

7.05 g of ethoxylated pentaerythritol tetraacrylate (av. mol. wt. 575) (0.012255 moles), 5.0 g of 4-piperazinoacetophenone (0.02451 moles), toluene 50 ml and 0.25 g 1,8-diazabicyclo(5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted 4-piperazinoacetophenone, and then the solvent was removed on a rotary evaporator to yield the product.

Product yield 12.04 g of a viscous slightly yellow liquid.
The product was analysed by IR, HPLC and LCMS.

COMPARATIVE EXAMPLE 1

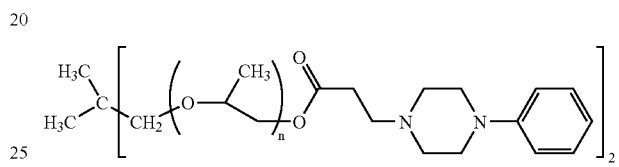

8.68 g Propoxylated neopentyl glycol diacrylate (PN-PGDA, mol. wt. 328), (0.026455 moles), 10.00 g N-phenylpiperazine (0.0595238 moles), toluene 150 ml and 0.60 g 1,8-diazabicyclo(5.4.0)undec-7-ene (DBU) (catalyst) were mixed in a two necked round bottomed flask equipped with a stirrer, condenser and temperature probe. The mixture was heated to reflux for a total of 10 hours (over 2 days). The mixture was then cooled and filtered to remove unreacted N-phenylpiperazine, and then the solvent was removed on the rotary evaporator to yield the product.

Product yield 18.82 g of a viscous slightly yellow liquid.
The product was analysed by IR, HPLC and LCMS.

EXAMPLE 16

The performance of the new materials was assessed in a black offset ink formulation based on a tri-functional urethane acrylate oligomer. A photoinitiator blend was added as 10% of the overall formulation, this comprised:

| | |
|---|---|
| 25% | Benzophenone |
| 25% | isopropylthioxanthone (ITX) |
| 30% | 2-ethylhexyl p-dimethylaminobenzoate (EHA) |
| 20% | piperazine derivative |

In the control formulation, the piperazine derivative was substituted by EHA giving an overall level of 50% EHA, as would be typical in a normal commercial formulation.

The inks were printed onto a carton board substrate (Incada Silk 260 gsm from Iggesund) to a density of approximately 1.8 using an IGT C1 print proofer. These were cured at 100 m/min using a Primarc Maxicure UV rig fitted with a single 300 W/inch medium pressure mercury lamp, operating at full or half power to provide good differentiation of results. The number of passes required to cure was measured using the "thumb twist test" and is shown in Table 1.

TABLE 1

Cure speed of inks containing piperazine derivatives

| Sensitiser | No. passes to cure | |
|---|---|---|
| | Half power | Full power |
| EHA | >12 | 6 |
| Comparative example 1 | >12 | 5 |
| Example 3 | 9, 9 | 4 |
| Example 4 | 7, 8 | 3 |
| Example 5 | 7, 7 | 3 |
| Example 6 | 6, 6 | 3 |
| Example 7 | 5, 6 | 3 |
| Example 8 | 6, 6 | 3 |
| Example 9 | 6, 7 | 3 |
| Example 11 | 4, 3 | 2 |
| Example 13 | 5, 4 | 2 |
| Example 14 | 7, 6 | 3 |
| Example 15 | 9, 9 | 4 |

The results in Table 1. show that, despite an addition level of only 20% (2% in the formulated ink), all the Examples boost the cure speed of the formulation significantly, particularly Example 11 and Example 13. Comparative Example 1 gives the same cure speed as the control formulation and demonstrates clearly that the enhanced performance of these novel materials comes from their photoinitiator/photosensitiser character and not as a source of abstractable hydrogen atoms, although in this respect they clearly have a similar reactivity to EHA. Example 15 has a similar structure to Example 9 but contains residual acrylate groups to give lower potential migration. Despite the relatively low photoinitiator functionality/gramme, Example 15 still shows a cure speed considerably faster than the standard formulation.

An additional ink was prepared using a photoinitiator composition of 35% of Example 4, 35% of Example 6 and 30% EHA, with the use of these two types of this compound class giving good light absorbance across the whole UV region, as shown in FIG. 1. Despite high levels of these piperazine derivatives, this ink required approximately 12 passes to cure at half power and 4 passes at full power. This result confirms that, although the products of this invention have some photoinitiator activity, the bulk of their benefit derives from their ability to sensitize benzophenone and benzophenone derivatives.

The invention claimed is:

1. A compound of formula (I):

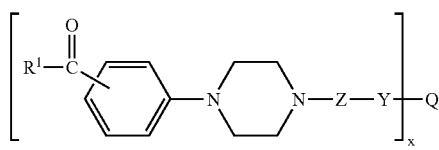

where:

$R^1$ represents a methyl group, an ethyl group, a $C_5$ or $C_6$ cycloalkyl group or a $C_6$-$C_{10}$ aryl group, said aryl group being unsubstituted or being substituted by at least one $C_1$-$C_4$ alkyl or $C_1$-$C_4$ alkoxy group;

Z represents a $C_6$-$C_{10}$ arylene group or a group of formula —$(CHR^4)_n$—, where $R^4$ represents a hydrogen atom, a hydroxy group or a $C_1$-$C_4$ alkyl group, and n is a number from 0 to 6;

Y represents a carbonyl group or a —$CH_2$— group, provided that $R^4$ represents a hydroxy group when Y represents a —$CH_2$— group;

Q represents a residue of a mono- or poly-hydroxy compound having from 1 to 6 hydroxy groups; and x is a number from 1 to 6; and esters thereof.

2. A compound according to claim 1, where Z represents a group of formula —$(CHR^4)_n$—, and n is 1.

3. A compound according to claim 2, in which $R^4$ represents a hydrogen atom, a methyl group or an ethyl group.

4. A compound according to claim 3, where $R^4$ represents a hydrogen atom.

5. A compound according to claim 2, in which n is a number from 2 to 6 and one group $R^4$ represents a hydrogen atom or a $C_1$-$C_4$ alkyl group, and the other or others of $R^4$ represent hydrogen atoms.

6. A compound according to claim 1, in which Z represents a phenylene group.

7. A compound according to claim 1, wherein Q represents a group of formula -Ax-Q', where:

A represents a group of formula —$[O(CHR^2CHR^3)_a]_y$—, —$[O(CH_2)_bCO]_y$— or —$[O(CH_2)_bCO]_{(y-1)}$—$[O(CHR^2CHR^3)_a]$—; where:

$R^2$ and $R^3$ are the same or different and each represents a hydrogen atom or a $C_1$-$C_4$ alkyl group;

a is a number from 1 to 2;

b is a number from 4 to 5; and y is a number from 1 to 10;

x is a number from 1 to 6; and

Q' represents a residue of a mono- or poly-hydroxy compound having from 1 to 6 hydroxy groups.

8. A compound according to claim 7, in which y is a number from 3 to 10.

9. A compound according to claim 8, in which A represents a group of formula —$[O(CHR^{13}CHR^{14})_a]_y$— where a is an integer from 1 to 2, and y is a number from 3 to 10.

10. A compound according to claim 8, in which A represents a group of formula —$[OCH_2CH_2]_y$—, —$[OCH_2CH_2CH_2CH_2]_y$— or —$[OCH(CH_3)CH_2]_y$—, where y is a number from 3 to 10.

11. A compound according to claim 8, in which A represents a group of formula —$[O(CH_2)_bCO]_y$—, where b is a number from 4 to 5 and y is a number from 3 to 10.

12. A compound according to claim 8, in which A represents a group of formula —$[O(CH_2)_bCO]_{(y-1)}$-$[O(CHR^2CHR^1)_a]$—, where a is a number from 1 to 2, b is a number from 4 to 5 and y is a number from 3 to 10.

13. A compound according to claim 7, in which x is 2 and y is a number from 1 to 10.

14. A compound according to claim 7, in which y is a number from 3 to 6.

15. A compound according to claim 7, in which the residue Q-(A-)$_x$ has a molecular weight no greater than 2000.

16. A compound according to claim 15, in which the residue Q'-(A-)$_x$ has a molecular weight no greater than 1200.

17. A compound according to claim 16, in which the residue Q'-(A-)$_x$ has a molecular weight no greater than 1000.

18. A compound according to claim 17, in which the residue Q'-(A-)$_x$ has a molecular weight no greater than 800.

19. A compound according to claim 7, in which Q' is a residue of a polyalkylene glycol, in which the alkylene part has from 2 to 6 carbon atoms.

20. A compound according to claim 7, in which Q' is a residue of ethylene glycol, propylene glycol, butylene glycol, glycerol, 2,2-propanediol, polyethylene glycol, polypropylene glycol, polybutylene glycol, trimethylolpropane, di-trimethylolpropane, pentaerythritol or di-pentaerythritol.

21. A compound according to any one of claim 6, in which x is 1.

22. A compound according to claim 20, in which Q is the residue of a compound of the formula $R^1$—OH.

23. A compound according to claim 21, in which Q is a $C_1$-$C_6$ alkoxy group or a phenoxy group.

24. A compound according to claim 21, in which Z is a phenylene group.

25. A compound according to claim 1, in which Q is a residue of a polyalkylene glycol, in which the alkylene part has from 2 to 6 carbon atoms.

26. A compound according to claim 25, in which Q is a residue of ethylene glycol, propylene glycol, butylene glycol, glycerol, 2,2-propanediol, polyethylene glycol, polypropylene glycol, polybutylene glycol, trimethylolpropane, ditrimethylolpropane, pentaerythritol or di-pentaerythritol.

27. An energy-curable composition comprising:
(a) a polymerisable monomer, prepolymer or oligomer;
(b) a photoinitiator; and
(c) a sensitiser which is a compound of formula (I), as claimed in claim 1, or an ester thereof.

28. A compound according to claim 7, in which Q' is trimethylopropane residue.

* * * * *